United States Patent [19]

Pissiotas et al.

[11] Patent Number: 4,917,721

[45] Date of Patent: Apr. 17, 1990

[54] HERBICIDAL ESTERS, COMPOSITIONS AND USE

[75] Inventors: Georg Pissiotas, Lörrach, Fed. Rep. of Germany; Hans Moser, Magden; Beat Böhner, Binningen, both of Switzerland

[73] Assignee: Ciba-Geigy Corporation, Ardsley, N.Y.

[21] Appl. No.: 10,927

[22] Filed: Feb. 5, 1987

[30] Foreign Application Priority Data

Feb. 11, 1986 [CH] Switzerland ............................. 535/86
Sep. 10, 1986 [CH] Switzerland .......................... 3637/86

[51] Int. Cl.$^4$ .................... A01N 43/38; C07D 209/48
[52] U.S. Cl. .......................................... 71/96; 548/513
[58] Field of Search .................... 548/476, 513; 71/96

[56] References Cited

U.S. PATENT DOCUMENTS

4,770,695  9/1988  Nagano et al. ........................ 71/96

FOREIGN PATENT DOCUMENTS

2150929  7/1985  United Kingdom .

OTHER PUBLICATIONS

Japanese Patent No. 60-109,563, 6-1985.
Patent Abstracts of Japan, vol. 8, No. 251, (C-252) 1984, 59-128371 (A).

*Primary Examiner*—Robert W. Ramsuer
*Attorney, Agent, or Firm*—Kevin T. Mansfield; Edward M. Roberts

[57] ABSTRACT

Novel 5-(N-3,4,5,6-tetrahydrophthalimido)benzoic acid esters of formula I below have good selective herbicidal properties pre- and postemergence and also influence or inhibit plant growth.

The novel compounds are of formula I

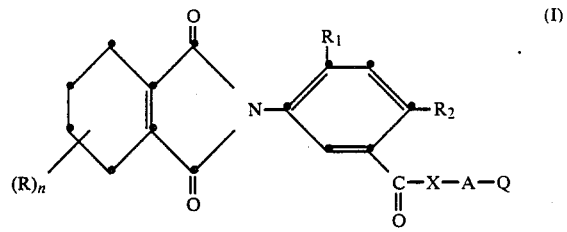

wherein
n is 0, 1 or 2,
R is $C_1$-$C_3$alkyl,
$R_1$ is hydrogen or halogen,
$R_2$ is halogen,
X is oxygen or sulfur,
A is a straight chain or branched $C_1$-$C_4$alkylene bridge,
Q is a 5- or 6-membered heterocycle which is bound through carbon or nitrogen and contains 1 to 3 hetero atoms and may further contain one or two carbonyl groups, which heterocycle may be fused to benzene rings and substituted by halogen, $C_1$-$C_4$alkyl, $C_1$-$C_3$haloalkyl, $C_1$-$C_3$alkoxy, $C_1$-$C_3$haloalkoxy, nitro, cyano, $C_1$-$C_3$alkylamino or di($C_1$-$C_3$)alkylamino, or Q is $C_1$-$C_4$alkylthio, $C_1$-$C_4$alkylsulfonyl, $C_2$-$C_8$alkoxyalkyl, nitro or di($C_1$-$C_4$)alkylamino, or is a benzyloxy, phenoxy or phenylthio radical, each of which may be substituted in the phenyl nucleus by halogen, $C_1$-$C_4$alkyl, $C_1$-$C_3$haloalkyl, $C_1$-$C_3$alkoxy, $C_1$-$C_3$haloalkoxy, nitro, cyano, $C_1$-$C_3$alkylamino or di($C_1$-$C_3$)alkylamino, or, if X is sulfur, Q may also be a $COOR_3$ radical, in which $R_3$ is $C_1$-$C_{20}$alkyl, $C_3$-$C_6$alkenyl, $C_3$-$C_6$alkynyl or $C_3$-$C_7$cycloalkyl, each of which is unsubstituted or substituted by halogen or $C_1$-$C_4$alkoxy.

4 Claims, No Drawings

HERBICIDAL ESTERS, COMPOSITIONS AND USE

The present invention relates to novel esters, namely 5-(N-3,4,5,6-tetrahydrophthalimido)benzoic acid esters of formula I with herbicidal and plant growth regulating properties, and to the preparation of these novel esters. The invention also relates to compositions which contain said novel componds and to the use thereof for selectively controlling weeds or for regulating plant growth.

The novel 5-(N-3,4,5,6-tetrahydrophthalimido)benzoic acid esters are of formula I

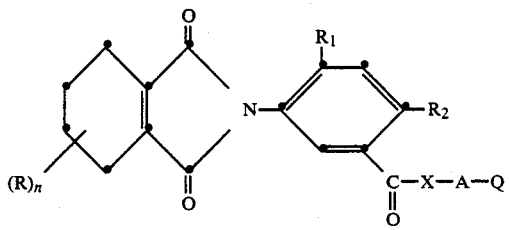

wherein
n is 0, 1 or 2,
R is $C_1$-$C_3$alkyl,
$R_1$ is hydrogen or halogen,
$R_2$ is halogen,
X is oxygen or sulfur,
A is a straight chain or branched $C_1$-$C_4$alkylene bridge,
Q is a 5- or 6-membered heterocycle which is bound through carbon or nitrogen and contains 1 to 3 hetero atoms and may further contain one or two carbonyl groups, which heterocycle may be fused to benzene rings and substituted by halogen, $C_1$-$C_4$alkyl, $C_1$-$C_3$haloalkyl, $C_1$-$C_3$alkoxy, $C_1$-$C_3$haloalkoxy, nitro, cyano, $C_1$-$C_3$alkylamino or di($C_1$-$C_3$)alkylamino, or Q is $C_1$-$C_4$alkylthio, $C_1$-$C_4$alkylsulfonyl, $C_2$-$C_8$alkoxyalkyl, nitro or di($C_1$-$C_4$)alkylamino, or is a benzyloxy, phenoxy or phenylthio radical, each of which may be substituted in the phenyl nucleus by halogen, $C_1$-$C_4$alkyl, $C_1$-$C_3$haloalkyl, $C_1$-$C_3$alkoxy, $C_1$-$C_3$haloalkoxy, nitro, cyano, $C_1$-$C_3$alkylamino or di($C_1$-$C_3$)alkylamino, or, if X is sulfur, Q may also be a $COOR_3$ radical, in which
$R_3$ is $C_1$-$C_{20}$alkyl, $C_3$-$C_6$alkenyl, $C_3$-$C_6$alkynyl or $C_3$-$C_7$cycloalkyl, each of which may be unsubstituted or substituted by halogen or $C_1$-$C_4$alkoxy.

The 5-(N-3,4,5,6-tetrahydrophthalimido)benzoic acid esters of formula I have herbicidal properties and can be employed for controlling weeds. Depending on the rate of application, they act as either total or selective herbicides and can be used for controlling weeds in crops of useful plants.

These compounds also have plant growth regulating properties and can be used for inhibiting plant growth.

Particularly active compounds are those in which
A, n, R, $R_1$, $R_2$ and X are as defined for formula I and Q is a 5- or 6-membered heterocycle which is bound through carbon or nitrogen and contains 1 to 3 hetero atoms and may further contain one or two carbonyl groups, which heterocycle may be fused to benzene rings and substituted by halogen, $C_1$-$C_4$alkyl, $C_1$-$C_3$haloalkyl, $C_1$-$C_3$alkoxy, $C_1$-$C_3$haloalkoxy, nitro, cyano, alkylamino or dialkylamino;

A, n, R and X are as defined for formula I and $R_1$ is hydrogen, chlorine or fluorine, $R_2$ is bromine or chlorine and Q is a 5- or 6-membered heterocyclic radical selected from the group consisting of furanyl, thienyl, pyrrolyl, pyrrolidinyl, piperazinyl, imidazolyl, triazolyl, thiazolyl, oxazolyl, thiadiazolyl, oxadiazolyl, pyridine, piperidine, oxazine, morpholino, pyrazolyl, quinolyl, benzazole, benzthiazolyl, benzimidazolyl and triazinyl, each of which radicals may contain one or two carbonyl groups and be substituted by halogen, $C_1$-$C_4$alkyl, $C_1$-$C_3$haloalkyl, $C_1$-$C_3$alkoxy, $C_1$-$C_3$haloalkoxy, nitro, cyano, $C_1$-$C_3$alkylamino or di($C_1$-$C_3$)alkylamino.

Compounds which are particularly effective are
furan-2-yl-methyl 5-(N-3,4,5,6-tetrahydrophthalimido)-2-chloro-4-fluorobenzoate,
pyridin-2-ylethyl 5-(N-3,4,5,6-tetrahydrophthalimido)-2-chloro-4-fluorobenzoate,
thien-2-ylethyl 5-(N-3,4,5,6-tetrahydrophthalimido)-2-chloro-4-fluorobenzoate,
4-methylthiazol-2-ylethyl 5-(N-3,4,5,6-tetrahydrophthalimido)-2-chloro-4-fluorobenzoate,
pyrrolidinoethyl 5-(N-3,4,5,6-tetrahydrophthalimido)-2-chloro-4-fluorobenzoate,
pyrrolidin-2-on-1-ylethyl 5-(N-3,4,5,6-tetrahydrophthalimido-2-chloro-4-fluorobenzoate and
morpholinoethyl 5-(N-3,4,5,6-tetrahydrophthalimido)-2-chloro-4-fluorobenzoate.

Compounds which are also very active are those in which
A, n, R, $R_1$, $R_2$ and X are as defined for formula I and Q is a $C_1$-$C_4$alkylthio group, in particular ethylthiomethyl 5-(N-3,4,5,6-tetrahydrophthalimido)-2-chloro-4-fluorobenzoate;

A, n, R, $R_1$ and $R_2$ are as defined for formula I and Q is the nitro group;

A, n, R, $R_1$ and $R_2$ are as defined for formula I and Q is a $C_2$-$C_8$alkoxycarbonyl group, in particular methoxycarbonylethyl 5-(N-3,4,5,6-tetrahydrophthalimido)-2-chloro-4-fluorobenzoate and butoxycarbonylbutyl 5-(N-3,4,5,6-tetrahydrophthalimido)-2-chloro-4-fluorobenzoate.

Compounds which also exhibit very good activity are those in which A, n, R, $R_1$, $R_2$ and X are as defined for formula I and Q is a benzyloxy, phenoxy, or phenylthio radical, each of which may be substituted in the phenyl nucleus by halogen, $C_1$-$C_4$alkyl, $C_1$-$C_3$haloalkyl, $C_1$-$C_3$alkoxy, $C_1$-$C_3$haloalkoxy, nitro, cyano, $C_1$-$C_3$alkylamino or di($C_1$-$C_3$)alkylamino, in particular phenylthioethyl 5-(N-3,4,5,6-tetrahydrophthalimido)-2-chloro-4-fluorobenzoate.

A further group of very active compounds comprises compounds of the formula Ia

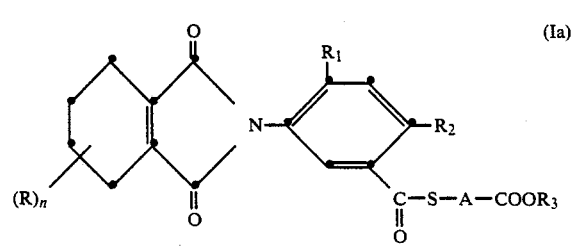

wherein A, n, R, $R_1$, $R_2$ and $R_3$ are as defined for formula I, in particular the compounds
1-isopropoxycarbonyleth-1-ylthio 5-(N-3,4,5,6-tetrahydrophthalimido)-2-chloro-4-fluorobenzoate, 1-ethoxycarbonyleth-1-ylthio 5-(N-3,4,5,6-tetrahydrophthalimido)-2-chloro-4-fluorobenzoate,
decyloxycarbonylmethylthio 5-(N-3,4,5,6-tetrahydrophthalimido)-2-chloro-b 4-fluorobenzoate,
cyclohexyloxycarbonylmethylthio 5-(N-3,4,5,6-tetrahydrophthalimido)-2-chloro-4-fluorobenzoate,
n-butoxycarbonylmethylthio 5-(N-3,4,5,6-tetrahydrophthalimido)-2-chloro-4-fluorobenzoate,
hept-3-yloxycarbonylmethylthio 5-(N-3,4,5,6-tetrahydrophthalimido)-2-chloro-4-fluorobenzoate,
methoxyethoxycarbonylmethylthio 5-(N-3,4,5,6-tetrahydrophthalimido)-2-chloro-4-fluorobenzoate,
methoxycarbonylmethylthio 5-(N-3,4,5,6-tetrahydrophthalimido)-2-chlorobenzoate,
ethoxycarbonyleth-1-ylthio 5-(N-3,4,5,6-tetrahydrophthalimido)-2-chlorobenzoate,
methoxyethoxycarbonylmelthylthio 5-(N-3,4,5,6-tetrahydrophthalimido)-2-chlorobenzoate,
n-butoxycarbonylmethylthio 5-(N-3,4,5,6-tetrahydrophthalimido)-2-chlorobenzoate,
isopropoxycarbonylmethylthio 5-(N-3,4,5,6-tetrahydrophthalimido)-2-chlorobenzoate,
cyclohexyloxycarbonylmethylthio 5-(N-3,4,5,6-tetrahydrophthalimido)-2-chlorobenzoate,
isoproxycarbonyleth-1-ylthio 5-(N-3,4,5,6-tetrahydrophthalimido)-2-chlorobenzoate,
methoxycarbonylmethylthio 5-(N-3,4,5,6-tetrahydrophthalimido)-2-chloro-4-fluorobenzoate,
isopropoxycarbonylmethylthio 5-(N-3,4,5,6-tetrahydrophthalimido)-2-chloro-4-fluorobenzoate,
ethoxycarbonylmethylthio 5-(N-3,4,5,6-tetrahydrophthalimido)-2-chloro-4-fluorobenzoate,
methoxycarbonyleth-1-ylthio 5-(N-3,4,5,6-tetrahydrophthalimido)-2-chlorobenzoate,
methoxycarbonyleth-1-ylthio 5-(N-3,4,5,6-tetrahydrophthalimido)-2-chloro-4-fluorobenzoate,
ethoxycarbonylmethylthio 5-(N-3,4,5,6-tetrahydrophthalimido)-2-chlorobenzoate,
allyloxycarbonyleth-1-ylthio 5-(N-3,4,5,6-tetrahydrophthalimido)-2-chloro-4-fluorobenzoate and
propinyloxycarbonylmethylthio 5-(N-3,4,5,6-tetrahydrophthalimido)-2-chloro-4-fluorobenzoate.

In accordance with the present invention, the novel 5(N-3,4,5,6-tetrahydrophthalimido)benzoic acid esters of formula I are prepared by reacting the anhydride of a 3,4,5,6-tetrahydrophthalic acid of formula II

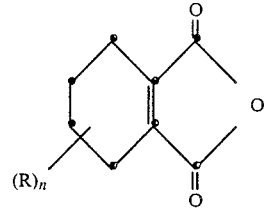

(II)

wherein R and n are as defined for formula I, with the equimolar amount of a derivative of a 3-aminobenzoic acid ester of formula III

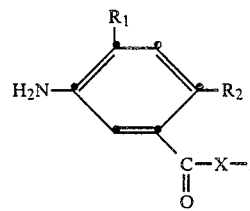

(III)

wherein A, $R_1$, $R_2$, X and Q are as defined for formula I, in an inert organic solvent or diluent and in the absence or presence of a minor amount of a dehydrating agent.

Suitable solvents or diluents for this reaction are higher boiling hydrocarbons, lower alkane acids and the esters thereof, higher boiling ketones and ethers. Examples of such solvents and diluents are toluene, xylene, acetic acid, ethyl acetate, isopropyl ether, tetrahydrofuran, methyl ethyl ketone and dimethylformamide.

The reaction takes place at a temperature in the range from room temperature to the boiling point of the reaction mixture.

In order to speed up the reaction, a minor amount of a dehydrating or water-absorbing agent may be added, e.g. of sulfuric acid or of an organic sulfonic acid, of a salt such as sodium acetate or of an anhydride such as phosphorus pentoxide.

The 3-aminobenzoic acid derivative of formula III can e.g. be prepared by the following synthesis route:

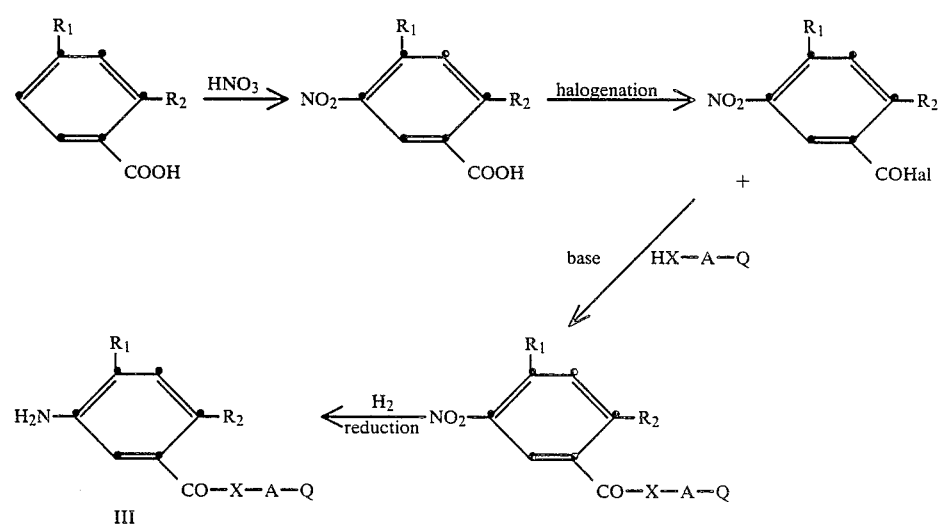

In the above formulae, $R_1$, $R_2$, X, A and Q are as defined for formula I.

A benzoic acid suitably substituted in the phenyl nucleus is nitrated with a nitric acid mixture and the resultant 3-nitrobenzoic acid is subsequently converted into the acid halide, e.g. with phosphoroxy chloride or bromide, thionyl chloride or bromide or sulfuryl chloride or bromide.

The acid halide thus obtained is then reacted with an alkanol of the formula HO—A—Q, in which A and Q are as defined for formula I, in the presence of the molar amount of a base.

However, the 3-nitrobenzoic acid derivative may also be condensed direct with an alkyl halide Hal—A—Q, in which A, X and Q are as defined for formula I and Hal is a halogen atom, preferably chlorine or bromine, in the presence of a base.

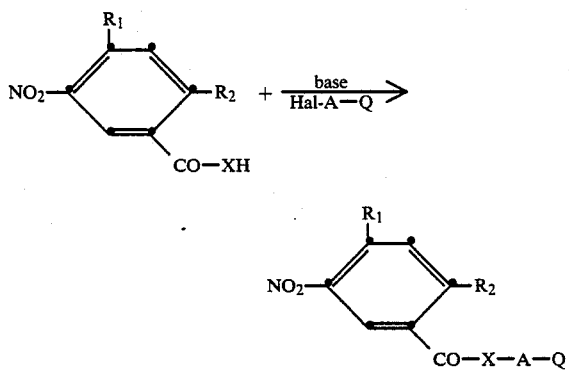

The resultant 3-nitrobenzoic acid ester is then reduced with hydrogen, e.g. in the presence of Raney nickel, to give the 3-aminobenzoic acid ester. The amine is subsequently condensed with a 3,4,5,6-tetrahydrophthalic anhydride in accordance with the process of this invention.

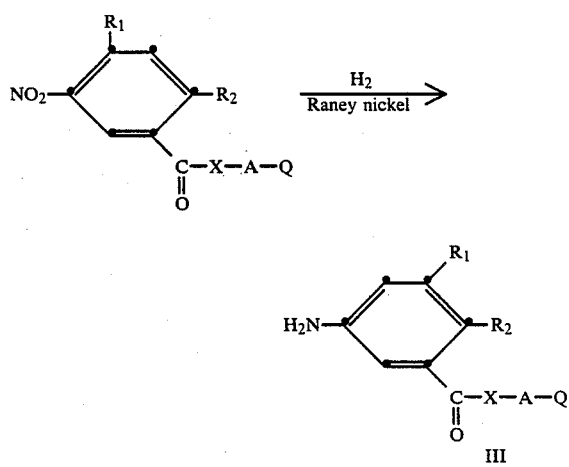

In accordance with a further process of the present invention, the 5-(N-3,4,5,6-tetrahydrophthalimido)benzoic acid esters of formula I according to claim 1 are obtained by reacting a 5-(N-3,4,5,6-tetrahydrophthalimido)benzoyl halide of formula V

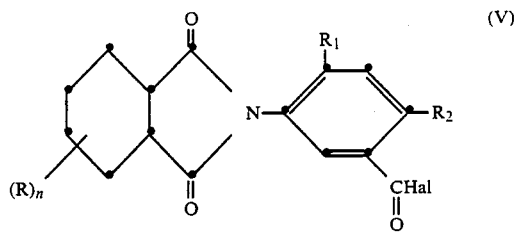

wherein n, R, $R_1$ and $R_2$ are as defined for formula I and Hal is a halogen atom, preferably chlorine or bromine, with an alkanol of formula VI $$HX—A—Q \qquad (VI)$$

wherein A, X and Q are as defined for formula I, in an inert organic solvent or diluent and in the presence of a base.

Higher boiling hydrocarbons, lower esters of alkane acids, higher boiling ketones and ethers are suitable solvents or diluents for this reaction too. Examples of such solvents and diluents are hexane, benzene, toluene, xylene, ethyl acetate, isopropyl ether, dioxane and methyl ethyl ketone.

The reaction takes place at a temperature in the range from 0° C. to the boiling point of the reaction mixture.

Suitable bases are secondary and tertiary amines, ammonium bases and the hydroxides, carbonates and bicarbonates of alkali metals, for example diethylamine, triethylamine, pyridine, collidine, sodium hydroxide, sodium carbonate, sodium bicarbonate and ammonia.

The 5-(N-3,4,5,6-tetrahydrophthalimido)benzoyl halide of formula V is prepared by condensing a phthalic anhydride of formula II with a 3-aminobenzoic acid suitably substituted by $R_1$ and $R_2$ and effecting subsequent halogenation in accordance with the described process.

A further process for the preparation of the 5-(N-3,4,5,6-tetrahydrophthalimido)benzoic acid esters of formula I comprises reacting a 5-(N-3,4,5,6-tetrahydrophthalimido)benzoic acid ester of formula VII

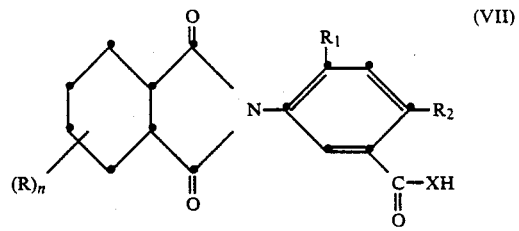

wherein n, R, $R_1$, $R_2$ and X are as defined for formula I, with an alkyl halide of formula VIII $$Hal—A—Q \qquad (VIII)$$

wherein A and Q are as defined in claim 1 and Hal is a halogen atom, preferably chlorine or bromine, in an inert organic solvent or diluent and in the presence of the molar amount of a base.

Suitable solvents or diluents are those listed under the first or second process.

The reaction takes place at a temperature in the range from 0° C. to the boiling point of the reaction mixture.

The above-mentioned secondary or tertiary amines, ammonium bases, hydroxides, carbonates or bicarbonates of alkali metals may be employed as bases for this reaction too.

The reaction conditions in all described variants are similar.

The compounds of formula I are usually successfully applied at concentrations of 0.05 to 4 kg/ha, in particular 0.1 to 1 kg/ha.

When used at low rates of application, the compounds of formula I have good selective growth inhibiting and selective herbicidal properties which make them most suitable for use in crops of useful plants, preferably in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of formula I are effective even when used at very low rates of application.

The compounds of formula I have in addition pronounced plant growth inhibiting properties. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth inhibitors resides in the fact that nutrients are able increasingly to promote flower formation and fruiting, whereas vegetative growth is inhibited.

The compounds of formula I can also be used for defoliating and desiccating crops of cotton and potatoes. By treating the crops at the moment of ripening, the harvesting of the cotton capsules or of the tubers is greatly facilitated when the leaves fall off and/or shrivel up or when the shrubs shrivel up.

At higher rates of application of compounds of formula I, all tested plants are so severely damaged in their development that they die.

The invention also relates to herbicidal and plant growth regulating compositions which contain a novel compound of formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, together with the adjuvants conventionally employed in the art of formulation, and are therefore formulated in known manner e.g. to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomelthyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/-polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch" (Handbook of Surfactants), C. Hanser Verlag, Munich & Vienna, 1981.

The pesticidal preparations usually contain 0.1 to 95%, preferably 0.1 to 80%, of a compound of formula I, 1 to 99.9% of a solid or liquid adjuvant, and 0 to 25%, preferably 0.1 to 25%, of a surfactant.

Preferred formulations are composed in particular of the following constituents (% = percentage by weight):

| Emulsifiable concentrates | |
|---|---|
| compound of formula I: | 1 to 20%, preferably 5 to 10% |
| surfactant: | 5 to 30%, preferably 10 to 20% |
| liquid carrier: | 50 to 94%, preferably 70 to 85% |
| Dusts | |
| compound of formula I: | 0.1 to 10%, preferably 0.1 to 1% |
| solid carrier: | 99.9 to 90%, preferably 99.9 to 99% |
| Suspension concentrates | |
| compound of formula I: | 5 to 75%, preferably 10 to 50% |
| water: | 94 to 25%, preferably 90 to 30% |
| surfactant: | 1 to 40%, preferably 2 to 30% |
| Wettable powders | |
| compound of formula I: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| compound of formula I: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001% of active ingredient. The rates of application are usually from 0.005 to 5 ka a.i./ha.

The compositions may also contain further ingredients such as stabilisers, antifoams, viscosity regulators, binders, tackifiers, as well as fertilisers and other compounds for obtaining special effects.

The following Example illustrates the preparation of an ester of formula I. Further compounds prepared in corresponding manner are listed in the subsequent Tables.

EXAMPLE 1

Preparation of pyridin-2-ylethyl 2-chloro-4-fluoro-5-(N-3,4,5,6-tetrahydrophthalimido)-benzoate

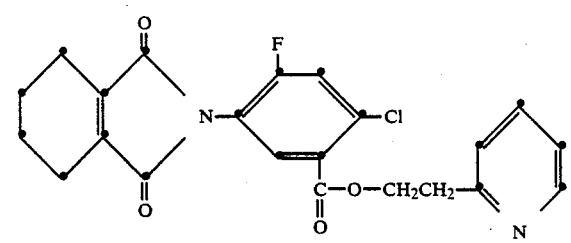

With stirring, 1.2 ml of triethylamine are slowly added dropwise to a mixture of 3.4 g of 2-chloro-4-fluoro-5-(N-3,4,5,6-tetrahydrophthalimido)benzoyl chloride, 1.2 ml of 2-(2-hydroxyethyl)pyridine and 30 ml of toluene. After stirring for 3 hours at room temperature, the reaction mixture is filtered. The filtrate is then concentrated by evaporation in vacuo, affording 3.4 g of the title product in the form of a pale oil with a refractive index $n_D^{23}$ of 1.5581.

The compounds in Tables 1 and 2 are prepared by a procedure analogous to that of this Example.

TABLE 1

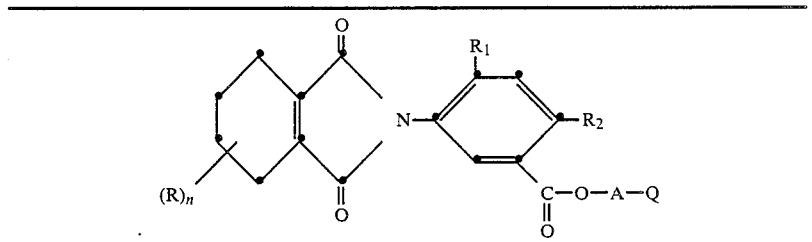

| No. | (R)$_n$ | R$_1$ | R$_2$ | A | Q | Physical data |
|---|---|---|---|---|---|---|
| 1.001 | — | F | Cl | CH$_2$ | 2-furyl | m.p. 120° C. |
| 1.002 | — | F | Cl | CH$_2$CH$_2$ | 2-pyridyl | n$_D^{23}$ 1.5581 |
| 1.003 | — | F | Cl | CH$_2$CH$_2$ | 4-methylthiazol-5-yl | n$_D^{23}$ 1.5654 |
| 1.004 | — | F | Cl | CH$_2$CH$_2$ | 2-thienyl | n$_D^{20}$ 1.5811 |
| 1.005 | — | F | Cl | CH$_2$CH$_2$ | SCH$_3$ | n$_D^{20}$ 1.5653 |
| 1.006 | — | F | Cl | CH$_2$CH$_2$ | pyrrolidin-2-on-1-yl | m.p. 109–111° C. |
| 1.007 | — | F | Cl | CH$_2$CH$_2$ | nC$_4$H$_9$OC$_4$H$_8$O | n$_D^{23}$ 1.5351 |
| 1.008 | — | F | Cl | CH$_2$CH$_2$ | pyrrolidino | n$_D^{21}$ 1.5560 |
| 1.009 | — | F | Cl | CH$_2$CH$_2$ | CH$_3$OC$_2$H$_4$O | n$_D^{21}$ 1.5489 |
| 1.010 | — | F | Cl | CH$_2$CH$_2$ | morpholino | n$_D^{23}$ 1.5514 |
| 1.011 | — | F | Cl | CH$_2$CH$_2$ | CH$_3$SO$_2$ | n$_D^{22}$ 1.5622 |
| 1.012 | — | F | Cl | CH$_2$CH$_2$ | phenylthio | n$_D^{27}$ 1.5850 |
| 1.013 | — | F | Cl | CH$_2$CH$_2$ | 2-furyl | |
| 1.014 | — | F | Cl | CH$_2$ | 2-tetrahydrofuryl | |
| 1.015 | — | F | Cl | CH$_2$CH$_2$ | 2-indolinyl | |
| 1.016 | — | F | Cl | CH$_2$CH$_2$ | 4-pyrazolyl | |
| 1.017 | — | F | Cl | CH$_2$CH$_2$ | 1-methyl-4-pyrazolyl | |
| 1.018 | — | F | Cl | CH$_2$CH$_2$CH$_2$ | 4-pyrazolyl | |
| 1.019 | — | F | Cl | CH$_2$CH$_2$CH$_2$ | 1-ethyl-4-pyrazolyl | |
| 1.020 | — | F | Cl | CH$_2$CH$_2$ | phthalimido | |
| 1.021 | — | F | Cl | CH$_2$CH$_2$CH$_2$ | 4-isoxazolyl | |
| 1.022 | — | F | Cl | CH$_2$CH$_2$ | 2-pyridin-2-yl | |
| 1.023 | — | F | Cl | CH$_2$ | 3-pyridinyl | |
| 1.024 | — | F | Cl | CH$_2$ | 4-pyridinyl | |
| 1.025 | — | F | Cl | CH$_2$CH$_2$ | 4-pyridinyl | |
| 1.026 | — | F | Cl | CH(CH$_3$) | 4-pyridinyl | |
| 1.027 | — | F | Cl | CH$_2$ | 3-pyridazinyl | |
| 1.028 | — | F | Cl | CH$_2$ | 1-pyrrolyl | |
| 1.029 | — | F | Cl | CH$_2$CH$_2$ | 1-pyrrolidinyl | |
| 1.030 | — | F | Cl | CH$_2$ | 1,2,4-triazol-1-yl | |
| 1.031 | — | F | Cl | CH$_2$CH$_2$ | 1,2,4-triazol-1-yl | |
| 1.032 | — | F | Cl | CH$_2$ | 1,3,4-triazol-1-yl | |
| 1.033 | — | F | Cl | CH$_2$CH$_2$ | 1,3;4-triazol-1-yl | |
| 1.034 | — | F | Cl | CH$_2$ | 4-imidazolyl | |
| 1.035 | — | F | Cl | CH$_2$CH$_2$ | 4-imidazolyl | |
| 1.036 | — | F | Cl | CH(CH$_3$) | 4-imidazolyl | |
| 1.037 | — | F | Cl | CH$_2$ | 2-imidazolyl | |
| 1.038 | — | F | Cl | CH$_2$CH$_2$ | 2-imidazolyl | |
| 1.039 | — | F | Cl | CH$_2$ | 2-methyl-4-imidazolyl | |
| 1.040 | — | F | Cl | CH$_2$ | 1-imidazolyl | |
| 1.041 | — | F | Cl | CH$_2$CH$_2$ | 1-imidazolyl | |
| 1.042 | — | F | Cl | CH(CH$_3$)CH$_2$ | 1-imidazolyl | m.p. 135–137° C. |
| 1.043 | — | F | Cl | CH$_2$CH$_2$ | NO$_2$ | |
| 1.044 | — | F | Cl | CH$_2$CH(CH$_3$)CH$_2$ | NO$_2$ | |
| 1.045 | — | F | Cl | CH$_2$CH$_2$ | 1-methylpyrrolidin-2-yl | |
| 1.046 | — | F | Cl | CH$_2$CH$_2$ | 2-piperidinyl | |
| 1.047 | — | F | Cl | CH$_2$ | benzyloxy | |
| 1.048 | — | F | Cl | CH$_2$CH$_2$ | phenoxy | n$_D^{22}$ 1.5757 |
| 1.049 | — | F | Cl | CH$_2$C(CH$_3$)$_2$ | phenoxy | |
| 1.050 | — | F | Cl | CH$_2$ | SCH$_3$ | |
| 1.051 | — | F | Cl | CH$_2$CH$_2$ | SOCH$_3$ | |
| 1.052 | — | F | Br | CH$_2$ | 2-tetrahydrofurfuryl | |
| 1.053 | — | F | Br | CH$_2$CH$_2$ | 2-indolinyl | |
| 1.054 | — | F | Br | CH$_2$CH$_2$ | 4-pyrazolyl | |
| 1.055 | — | F | Br | CH$_2$CH$_2$ | 1-methyl-4-pyrazolyl | |
| 1.056 | — | F | Br | CH$_2$CH$_2$CH$_2$ | 4-pyrazolyl | |
| 1.057 | — | F | Br | CH$_2$CH$_2$CH$_2$ | 1-ethyl-4-pyrazolyl | |
| 1.058 | — | F | Br | CH$_2$CH$_2$ | phthalimido | |
| 1.059 | — | F | Br | CH$_2$CH$_2$CH$_2$ | 4-isooxazolyl | |
| 1.060 | — | F | Br | CH$_2$CH$_2$ | 2-pyridin-2-yl | |
| 1.061 | — | F | Br | CH$_2$ | 3-pyridinyl | |
| 1.062 | — | F | Br | CH$_2$ | 4-pyridinyl | |
| 1.063 | — | F | Br | CH$_2$CH$_2$ | 4-pyridinyl | |
| 1.064 | — | F | Br | CH(CH$_3$) | 4-pyridinyl | |
| 1.065 | — | F | Br | CH$_2$ | 3-pyridazinyl | |
| 1.066 | — | F | Br | CH$_2$ | 1-pyrrolyl | |
| 1.067 | — | F | Br | CH$_2$CH$_2$ | 1-pyrrolidinyl | |
| 1.068 | — | F | Br | CH$_2$ | 1,2,4-triazol-1-yl | |
| 1.069 | — | F | Br | CH$_2$CH$_2$ | 1,2,4-triazol-1-yl | |

TABLE 1-continued

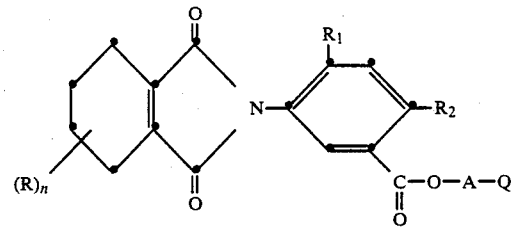

| No. | (R)$_n$ | R$_1$ | R$_2$ | A | Q | Physical data |
|---|---|---|---|---|---|---|
| 1.070 | — | F | Br | CH$_2$ | 1,3,4-triazol-1-yl | |
| 1.071 | — | F | Br | CH$_2$CH$_2$ | 1,3,4-triazol-1-yl | |
| 1.072 | — | F | Br | CH$_2$ | 4-imidazolyl | |
| 1.073 | — | F | Br | CH$_2$CH$_2$ | 4-imidazolyl | |
| 1.074 | — | F | Br | CH(CH$_3$) | 4-imidazolyl | |
| 1.075 | — | F | Br | CH$_2$ | 2-imidazolyl | |
| 1.076 | — | F | Br | CH$_2$CH$_2$ | 2-imidazolyl | |
| 1.077 | — | F | Br | CH$_2$ | 2-methyl-4-imidazolyl | |
| 1.078 | — | F | Br | CH$_2$ | 1-imidazolyl | |
| 1.079 | — | F | Br | CH$_2$CH$_2$ | 1-imidazolyl | |
| 1.080 | — | F | Br | CH(CH$_3$)CH$_2$ | 1-imidazolyl | m.p. 156–158° C. |
| 1.081 | — | F | Br | CH$_2$CH$_2$ | NO$_2$ | |
| 1.082 | — | F | Br | CH$_2$CH(CH$_3$)CH$_2$ | NO$_2$ | |
| 1.083 | — | F | Br | CH$_2$CH$_2$ | 1-methylpyrrolidin-2-yl | |
| 1.084 | — | F | Br | CH$_2$CH$_2$ | 2-piperidinyl | |
| 1.085 | — | F | Br | CH$_2$ | benzyloxy | |
| 1.086 | — | F | Br | CH$_2$CH$_2$ | phenoxy | |
| 1.087 | — | F | Br | CH$_2$C(CH$_3$)$_2$ | phenoxy | |
| 1.088 | — | F | Br | CH$_2$ | SCH$_3$ | |
| 1.089 | — | F | Br | CH$_2$CH$_2$ | SOCH$_3$ | |
| 1.090 | — | H | Cl | CH$_2$ | 2-tetrahydrofurfuryl | |
| 1.091 | — | H | Cl | CH$_2$CH$_2$ | 2-indolinyl | |
| 1.092 | — | H | Cl | CH$_2$CH$_2$ | 4-pyrazolyl | |
| 1.093 | — | H | Cl | CH$_2$CH$_2$ | 1-methyl-4-pyrazolyl | |
| 1.094 | — | H | Cl | CH$_2$CH$_2$CH$_2$ | 4-pyrazolyl | |
| 1.095 | — | H | Cl | CH$_2$CH$_2$CH$_2$ | 1-ethyl-4-pyrazolyl | |
| 1.096 | — | H | Cl | CH$_2$CH$_2$ | phthalimido | |
| 1.097 | — | H | Cl | CH$_2$CH$_2$CH$_2$ | 4-isooxazolyl | |
| 1.098 | — | H | Cl | CH$_2$CH$_2$ | 2-pyridin-2-yl | n$_D^{22}$ 1.5907 |
| 1.099 | — | H | Cl | CH$_2$ | 3-pyridinyl | |
| 1.100 | — | H | Cl | CH$_2$ | 4-pyridinyl | |
| 1.101 | — | H | Cl | CH$_2$CH$_2$ | 4-pyridinyl | |
| 1.102 | — | H | Cl | CH(CH$_3$) | 4-pyridinyl | |
| 1.103 | — | H | Cl | CH$_2$ | 3-pyridazinyl | |
| 1.104 | — | H | Cl | CH$_2$ | 1-pyrrolyl | |
| 1.105 | — | H | Cl | CH$_2$CH$_2$ | 1-pyrrolidinyl | |
| 1.106 | — | H | Cl | CH$_2$ | 1,2,4-triazol-1-yl | |
| 1.107 | — | H | Cl | CH$_2$CH$_2$ | 1,2,4-triazol-1-yl | |
| 1.108 | — | H | Cl | CH$_2$ | 1,3,4-triazol-1-yl | |
| 1.109 | — | H | Cl | CH$_2$CH$_2$ | 1,3,4-triazol-1-yl | |
| 1.110 | — | H | Cl | CH$_2$ | 4-imidazolyl | |
| 1.111 | — | H | Cl | CH$_2$CH$_2$ | 4-imidazolyl | |
| 1.112 | — | H | Cl | CH(CH$_3$) | 4-imidazolyl | |
| 1.113 | — | H | Cl | CH$_2$ | 2-imidazolyl | |
| 1.114 | — | H | Cl | CH$_2$CH$_2$ | 2-imidazolyl | |
| 1.115 | — | H | Cl | CH$_2$ | 2-methyl-4-imidazolyl | |
| 1.116 | — | H | Cl | CH$_2$ | 1-imidazolyl | |
| 1.117 | — | H | Cl | CH$_2$CH$_2$ | 1-imidazolyl | |
| 1.118 | — | H | Cl | CH(CH$_3$)CH$_2$ | 1-imidazolyl | |
| 1.119 | — | H | Cl | CH$_2$CH$_2$ | NO$_2$ | |
| 1.120 | — | H | Cl | CH$_2$CH(CH$_3$)CH$_2$ | NO$_2$ | |
| 1.121 | — | H | Cl | CH$_2$CH$_2$ | 1-methylpyrrolidin-2-yl | |
| 1.122 | — | H | Cl | CH$_2$CH$_2$ | 2-piperidinyl | |
| 1.123 | — | H | Cl | CH$_2$ | benzyloxy | |
| 1.124 | — | H | Cl | CH$_2$CH$_2$ | phenoxy | |
| 1.125 | — | H | Cl | CH$_2$C(CH$_3$)$_2$ | phenoxy | |
| 1.126 | — | H | Cl | CH$_2$ | SCH$_3$ | |
| 1.127 | — | H | Cl | CH$_2$CH$_2$ | SOCH$_3$ | |
| 1.128 | — | H | Cl | CH$_2$ | 2-furyl | |
| 1.129 | — | H | Cl | CH$_2$CH$_2$ | 2-pyridinyl | |
| 1.130 | — | H | Cl | CH$_2$CH$_2$ | 4-methylthiazol-5-yl | |
| 1.131 | — | H | Cl | CH$_2$CH$_2$ | 2-thienyl | |
| 1.132 | — | H | Cl | CH$_2$CH$_2$ | SCH$_3$ | |
| 1.133 | — | H | Cl | CH$_2$CH$_2$ | 1-piperdin-2-one | |
| 1.134 | — | H | Cl | CH$_2$CH$_2$ | nC$_4$H$_9$OC$_4$H$_8$O | |
| 1.135 | — | H | Cl | CH$_2$CH$_2$ | 1-morpholino | |
| 1.136 | — | H | Cl | CH$_2$CH$_2$ | SO$_2$CH$_3$ | |
| 1.137 | — | H | Cl | CH$_2$CH$_2$ | phenylthio | n$_D^{22}$ 1.6097 |
| 1.138 | — | H | Cl | CH$_2$CH$_2$ | piperidino | |

TABLE 1-continued

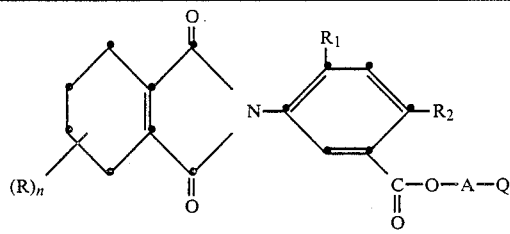

| No. | (R)$_n$ | R$_1$ | R$_2$ | A | Q | Physical data |
|---|---|---|---|---|---|---|
| 1.139 | — | H | Cl | CH$_2$CH$_2$ | CH$_3$OC$_2$H$_4$O | |
| 1.140 | — | Cl | Cl | CH$_2$ | 2-furyl | |
| 1.141 | — | Cl | Cl | CH$_2$CH$_2$ | 2-pyridinyl | m.p. 105–106° C. |
| 1.142 | — | Cl | Cl | CH$_2$CH$_2$ | 4-methylthiazol-5-yl | |
| 1.143 | — | Cl | Cl | CH$_2$CH$_2$ | 2-thienyl | |
| 1.144 | — | Cl | Cl | CH$_2$CH$_2$ | SCH$_3$ | |
| 1.145 | — | Cl | Cl | CH$_2$CH$_2$ | 1-piperdin-2-one | |
| 1.146 | — | Cl | Cl | CH$_2$CH$_2$ | nC$_4$H$_9$OC$_4$H$_8$O | |
| 1.147 | — | Cl | Cl | CH$_2$CH$_2$ | 1-morpholino | |
| 1.148 | — | Cl | Cl | CH$_2$CH$_2$ | SO$_2$CH$_3$ | |
| 1.149 | — | Cl | Cl | CH$_2$CH$_2$ | phenylthio | |
| 1.150 | — | Cl | Cl | CH$_2$CH$_2$ | piperidino | |
| 1.151 | — | Cl | Cl | CH$_2$CH$_2$ | CH$_3$OC$_2$H$_4$O | |
| 1.152 | — | H | Br | CH$_2$ | 2-furyl | |
| 1.153 | — | H | Br | CH$_2$CH$_2$ | 2-pyridinyl | |
| 1.154 | — | H | Br | CH$_2$CH$_2$ | 4-methylthiazol-5-yl | |
| 1.155 | — | H | Br | CH$_2$CH$_2$ | 2-thienyl | |
| 1.156 | — | H | Br | CH$_2$CH$_2$ | SCH$_3$ | |
| 1.157 | — | H | Br | CH$_2$CH$_2$ | 1-piperdin-2-one | |
| 1.158 | — | H | Br | CH$_2$CH$_2$ | nC$_4$H$_9$OC$_4$H$_8$O | |
| 1.159 | — | H | Br | CH$_2$CH$_2$ | 1-morpholino | |
| 1.160 | — | H | Br | CH$_2$CH$_2$ | SO$_2$CH$_3$ | |
| 1.161 | — | H | Br | CH$_2$CH$_2$ | phenylthio | |
| 1.162 | — | H | Br | CH$_2$CH$_2$ | piperidino | |
| 1.163 | — | H | Br | CH$_2$CH$_2$ | CH$_3$OC$_2$H$_4$O | |
| 1.164 | 3-CH$_3$ | F | Cl | CH$_2$ | 2-furyl | |
| 1.165 | 3-CH$_3$ | F | Cl | CH$_2$CH$_2$ | 2-pyridinyl | |
| 1.166 | 3-CH$_3$ | F | Cl | CH$_2$CH$_2$ | 4-methylthiazol-5-yl | |
| 1.167 | 3-CH$_3$ | F | Cl | CH$_2$CH$_2$ | 2-thienyl | |
| 1.168 | 3-CH$_3$ | F | Cl | CH$_2$CH$_2$ | SCH$_3$ | |
| 1.169 | 3-CH$_3$ | F | Cl | CH$_2$CH$_2$ | 1-piperdin-2-one | |
| 1.170 | 3-CH$_3$ | F | Cl | CH$_2$CH$_2$ | nC$_4$H$_9$OC$_2$H$_4$O | |
| 1.171 | 3-CH$_3$ | F | Cl | CH$_2$CH$_2$ | 1-morpholino | |
| 1.172 | 3-CH$_3$ | F | Cl | CH$_2$CH$_2$ | SO$_2$CH$_3$ | |
| 1.173 | 3-CH$_3$ | F | Cl | CH$_2$CH$_2$ | phenylthio | |
| 1.174 | 3-CH$_3$ | F | Cl | CH$_2$CH$_2$ | piperidino | |
| 1.175 | 3-CH$_3$ | F | Cl | CH$_2$CH$_2$ | CH$_3$OC$_2$H$_4$O | |
| 1.176 | 3-CH$_3$ | H | Cl | CH$_2$ | 2-furyl | |
| 1.177 | 3-CH$_3$ | H | Cl | CH$_2$CH$_2$ | 2-pyridinyl | |
| 1.178 | 3-CH$_3$ | H | Cl | CH$_2$CH$_2$ | 4-methylthiazol-5-yl | |
| 1.179 | 3-CH$_3$ | H | Cl | CH$_2$CH$_2$ | 2-thienyl | |
| 1.180 | 3-CH$_3$ | H | Cl | CH$_2$CH$_2$ | SCH$_3$ | |
| 1.181 | 3-CH$_3$ | H | Cl | CH$_2$CH$_2$ | 1-piperdin-2-one | |
| 1.182 | 3-CH$_3$ | H | Cl | CH$_2$CH$_2$ | nC$_4$H$_9$OC$_4$H$_8$O | |
| 1.183 | 3-CH$_3$ | H | Cl | CH$_2$CH$_2$ | 1-morpholino | |
| 1.184 | 3-CH$_3$ | H | Cl | CH$_2$CH$_2$ | SO$_2$CH$_3$ | |
| 1.185 | 3-CH$_3$ | H | Cl | CH$_2$CH$_2$ | phenylthio | |
| 1.186 | 3-CH$_3$ | H | Cl | CH$_2$CH$_2$ | piperidino | |
| 1.187 | 3-CH$_3$ | H | Cl | CH$_2$CH$_2$ | CH$_3$OC$_2$H$_4$O | |
| 1.188 | — | F | F | CH$_2$ | 2-furyl | |
| 1.189 | — | F | F | CH$_2$CH$_2$ | 2-pyridinyl | |
| 1.190 | — | F | F | CH$_2$CH$_2$ | 4-methylthiazol-5-yl | |
| 1.191 | — | F | F | CH$_2$CH$_2$ | 2-thienyl | |
| 1.192 | — | F | F | CH$_2$CH$_2$ | SCH$_3$ | |
| 1.193 | — | F | F | CH$_2$CH$_2$ | 1-piperdin-2-one | |
| 1.194 | — | F | F | CH$_2$CH$_2$ | nC$_4$H$_9$OC$_4$H$_8$O | |
| 1.195 | — | F | F | CH$_2$CH$_2$ | 1-morpholino | |
| 1.196 | — | F | F | CH$_2$CH$_2$ | SO$_2$CH$_3$ | |
| 1.197 | — | F | F | CH$_2$CH$_2$ | phenylthio | |
| 1.198 | — | F | F | CH$_2$CH$_2$ | piperidino | |
| 1.199 | — | F | F | CH$_2$CH$_2$ | CH$_3$OC$_2$H$_4$O | |
| 1.200 | — | F | Cl | CH$_2$ | furan-2-yl | m.p. 120° C. |
| 1.201 | — | H | Cl | CH(CH$_3$)CH$_2$ | pyrazol-1-yl | $n_D^{23}$ 1.5724 |
| 1.202 | — | F | Cl | C$_2$H$_4$ | pyrazol-1-yl | $n_D^{23}$ 1.5643 |
| 1.203 | — | F | Cl | CH(CH$_3$)CH$_2$ | pyrazol-1-yl | $n_D^{23}$ 1.5638 |
| 1.204 | — | F | Cl | CH(CH$_3$) | 1,2,4-triazol-1-yl | m.p. 97–99° C. |
| 1.205 | — | F | Cl | C$_2$H$_4$ | p-tolylthio | $n_D^{25}$ 1.5963 |
| 1.206 | — | H | Cl | C$_2$H$_4$ | p-tolylthio | $n_D^{22}$ 1.6069 |

TABLE 1-continued

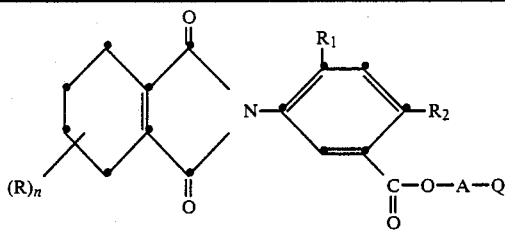

| No. | (R)$_n$ | R$_1$ | R$_2$ | A | Q | Physical data |
|---|---|---|---|---|---|---|
| 1.207 | — | F | Cl | CH(CH$_3$)CH$_2$ | phenylthio | n$_D^{25}$ 1.5915 |
| 1.208 | — | F | Cl | C$_3$H$_6$ | 1-methylpyrazol-4-yl | resin |
| 1.209 | — | F | Cl | CH(CH$_3$)CH$_2$ | phenoxy | n$_D^{22}$ 1.5638 |
| 1.210 | — | H | Cl | CH(CH$_3$)CH$_2$ | phenoxy | m.p. 150–152° C. |
| 1.211 | — | H | Cl | CH(CH$_3$)CH$_2$ | p-tolylthio | n$_D^{21}$ 1.5836 |
| 1.212 | — | F | Cl | CH(CH$_3$)CH$_2$ | 2,4-dichlorophenoxy | n$_D^{21}$ 1.5654 |
| 1.213 | — | F | Cl | CH(CH$_3$)CH$_2$ | 4-chlorophenylthio | m.p. 92–94° C. |
| 1.214 | — | H | Cl | CH(CH$_3$)CH$_2$ | phenylthio | n$_D^{23}$ 1.5991 |
| 1.215 | — | F | Cl | CH(CH$_3$)CH$_2$ | 4-methoxyphenylthio | n$_D^{23}$ 1.5712 |
| 1.216 | — | F | Br | CH(CH$_3$)CH$_2$ | 4-chlorophenylthio | resin |
| 1.217 | — | F | Cl | CH(CH$_3$)CH$_2$ | ethylthio | n$_D^{27}$ 1.5549 |
| 1.218 | — | F | Cl | CH(CH$_3$)CH$_2$ | tert-butylthio | n$_D^{27}$ 1.5250 |
| 1.219 | — | F | Cl | CH(CH$_3$)CH$_2$ | methylthio | n$_D^{25}$ 1.5615 |
| 1.220 | — | F | Cl | CH(CH$_3$)CH$_2$ | isopropylthio | n$_D^{25}$ 1.5857 |
| 1.221 | — | F | Br | CH(CH$_3$)CH$_2$ | phenylthio | m.p. 106–108° C. |
| 1.222 | — | F | Br | C$_2$H$_4$ | phenylthio | n$_D^{23}$ 1.6551 |
| 1.223 | — | H | Cl | C$_2$H$_4$ | pyrazol-1-yl | m.p. 105–107° C. |
| 1.224 | — | F | Cl | CH(CH$_3$)CH$_2$ | N(CH$_3$)$_2$ | n$_D^{24}$ 1.5463 |
| 1.225 | — | F | Br | CH(CH$_3$)CH$_2$ | N(CH$_3$)$_2$ | n$_D^{24}$ 1.5559 |
| 1.226 | — | F | Cl | CH(CH$_3$)CH$_2$ | N(C$_2$H$_5$)$_2$ | n$_D^{24}$ 1.5338 |

TABLE 2

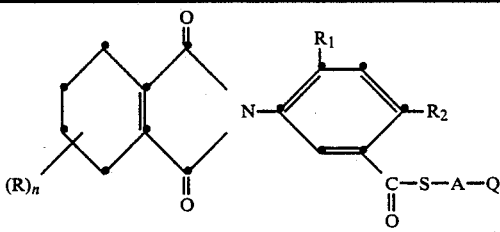

| No. | (R)$_n$ | R$_1$ | R$_2$ | A | Q | Physical data |
|---|---|---|---|---|---|---|
| 2.001 | — | F | Cl | CH(CH$_3$) | COOCH(CH$_3$)$_2$ | n$_D^{23}$ 1.5421 |
| 2.002 | — | F | Cl | CH(CH$_3$) | COOC$_2$H$_5$ | n$_D^{23}$ 1.5357 |
| 2.003 | — | F | Cl | CH$_2$ | COO(CH$_2$)$_{17}$CH$_3$ | wax-like |
| 2.004 | — | F | Cl | CH$_2$ | COO(CH$_2$)$_9$CH$_3$ | n$_D^{24}$ 1.5254 |
| 2.005 | — | F | Cl | CH$_2$ | COOcyclohexyl | n$_D^{24}$ 1.5519 |
| 2.006 | — | F | Cl | CH$_2$ | COO(CH$_2$)$_{15}$CH$_3$ | n$_D^{24}$ 1.5207 |
| 2.007 | — | F | Cl | CH$_2$ | COO(CH$_2$)$_{11}$CH$_3$ | n$_D^{24}$ 1.5274 |
| 2.008 | — | F | Cl | CH$_2$ | COOC$_4$H$_9$n | n$_D^{24}$ 1.5525 |
| 2.009 | — | F | Cl | CH$_2$ | COOCH(C$_2$H$_5$)C$_4$H$_9$n | n$_D^{24}$ 1.5388 |
| 2.010 | — | F | Cl | CH$_2$ | COOC$_2$H$_4$OCH$_3$ | n$_D^{24}$ 1.5542 |
| 2.011 | — | H | Cl | CH$_2$ | COOCH$_3$ | n$_D^{24}$ 1.5832 |
| 2.012 | — | H | Cl | CH(CH$_3$) | COOC$_2$H$_5$ | n$_D^{24}$ 1.5712 |
| 2.013 | — | H | Cl | CH$_2$ | COOC$_2$H$_4$OCH$_3$ | n$_D^{24}$ 1.5662 |
| 2.014 | — | H | Cl | CH$_2$ | COOCH(C$_2$H$_5$)C$_4$H$_9$n | n$_D^{24}$ 1.5431 |
| 2.015 | — | H | Cl | CH$_2$ | COOC$_4$H$_9$n | n$_D^{24}$ 1.5639 |
| 2.016 | — | H | Cl | CH$_2$ | COO(CH$_2$)$_9$CH$_3$ | n$_D^{24}$ 1.5425 |
| 2.017 | — | H | Cl | CH$_2$ | COO(CH$_2$)$_{11}$CH$_3$ | n$_D^{24}$ 1.5342 |
| 2.018 | — | H | Cl | CH$_2$ | COOCH(CH$_3$)$_2$ | n$_D^{24}$ 1.5659 |
| 2.019 | — | H | Cl | CH$_2$ | COO(CH$_2$)$_{15}$CH$_3$ | n$_D^{24}$ 1.5292 |
| 2.020 | — | H | Cl | CH$_2$ | COO(CH$_2$)$_{17}$CH$_3$ | n$_D^{24}$ 1.5415 |
| 2.021 | — | H | Cl | CH$_2$ | COOcyclohexyl | n$_D^{24}$ 1.5545 |
| 2.022 | — | H | Cl | CH(CH$_3$) | COOCH(CH$_3$)$_2$ | n$_D^{24}$ 1.5532 |
| 2.023 | — | F | Cl | CH$_2$ | COOCH$_3$ | n$_D^{23}$ 1.5532 |
| 2.024 | — | F | Cl | CH$_2$ | COOCH(CH$_3$)$_2$ | n$_D^{20}$ 1.5623 |
| 2.025 | — | F | Cl | CH$_2$ | COOC$_2$H$_5$ | n$_D^{22}$ 1.5638 |
| 2.026 | — | H | Cl | CH(CH$_3$) | COOCH$_3$ | n$_D^{21}$ 1.5703 |
| 2.027 | — | F | Cl | CH(CH$_3$) | COOCH$_3$ | n$_D^{22}$ 1.5472 |
| 2.028 | — | H | Cl | CH$_2$ | COOC$_2$H$_5$ | n$_D^{25}$ 1.5720 |
| 2.029 | — | F | Cl | CH$_2$ | COOCH$_2$CH=CH$_2$ | |
| 2.030 | — | F | Cl | CH(CH$_3$) | COOCH$_2$CH=CH$_2$ | |
| 2.031 | — | H | Cl | CH$_2$ | COOCH$_2$CH=CH$_2$ | |
| 2.032 | — | H | Cl | CH(CH$_3$) | COOCH$_2$CH=CH$_2$ | |

TABLE 2-continued

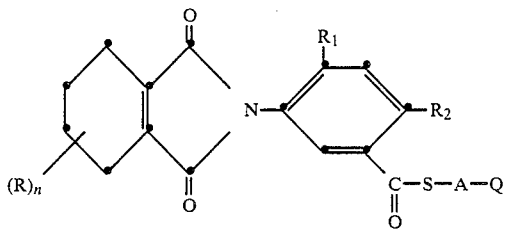

| No. | $(R)_n$ | $R_1$ | $R_2$ | A | Q | Physical data |
|---|---|---|---|---|---|---|
| 2.033 | — | F | Cl | $CH_2$ | $COOCH_2C\equiv CH$ | |
| 2.034 | — | F | Cl | $CH(CH_3)$ | $COOCH_2C\equiv CH$ | |
| 2.035 | — | H | Cl | $CH_2$ | $COOCH_2C\equiv CH$ | |
| 2.036 | — | H | Cl | $CH(CH_3)$ | $COOCH_2C\equiv CH$ | |
| 2.037 | — | H | Cl | $CH(CH_3)$ | $COOCH(CH_3)_2$ | $n_D^{24}$ 1.5532 |
| 2.038 | — | F | Cl | $CH(CH_3)$ | $C_2H_5$ | $n_D^{37}$ 1.5861 |
| 2.039 | — | F | Br | $CH(CH_3)$ | $COOC_2H_5$ | $n_D^{36}$ 1.5571 |
| 2.040 | — | F | Br | $CH_2$ | $COOCH_3$ | $n_D^{25}$ 1.5814 |
| 2.041 | — | F | Br | $CH_2$ | $COOC_2H_5$ | $n_D^{25}$ 1.5622 |
| 2.042 | — | F | Br | $CH_2$ | $COOC_3H_7i$-iso | $n_D^{25}$ 1.5611 |
| 2.043 | — | F | Br | $CH(CH_3)$ | $COOCH_3$ | $n_D^{25}$ 1.5708 |
| 2.044 | — | F | Br | $CH(CH_3)$ | $COOC_3H_7i$-iso | $n_D^{25}$ 1.5623 |
| 2.045 | — | F | Br | $CH_2$ | $COOC_2H_4OCH_3$ | $n_D^{23}$ 1.5750 |
| 2.046 | — | F | Br | $CH_2$ | $COOC_4H_9n$ | $n_D^{21}$ 1.5667 |

Formulation Examples

EXAMPLE 2

Formulation Examples for compounds of formula I (percentages are by weight)

| (a) Wettable powders | (a) | (b) | (c) |
|---|---|---|---|
| compound of Tables 1 and 2 | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| compound of Tables 1 and 2 | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| compound of Tables 1 and 2 | 0.1% | 1% |
| talcum | 99.9% | — |
| kaolin | — | 99% |

Dusts which are ready for use are obtained by mixing the active ingredient with the carrier, and grinding the mixture in a suitable mill.

| (d) Extruder granulates | (a) | (b) |
|---|---|---|
| compound of Tables 1 and 2 | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| compound of Tables 1 and 2 | 3% |
| polyethylene glycol (mol. wt. 200) | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrates | (a) | (b) |
|---|---|---|
| compound of Tables 1 and 2 | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| compound of Tables 1 and 2 | 5% |
| isopropylamine | 1% |
| octylphenol polyethylene glycol ether (78 moles of ethylene oxide) | 3% |
| water | 91% |

Biological Examples

EXAMPLE 3

Preemergence herbicidal action

In a greenhouse, immediately after sowing the test plants in seed dishes, the surface of the soil is treated with an aqueous dispersion of the test compounds, obtained from a 25% emulsifiable concentrate. Concentrations of 4 kg of test compound per hectare are applied. The seed dishes are kept in the greenhouse at 22°–25° C. and 50–70% relative humidity and the test is evaluated 3 weeks later. The state of the plants is assessed accordance with the following rating:

1: plant has died or it has not germinated
2–4: severe damage (the higher the grade, the less severe the damage)
5: moderate damage
6–8: slight damage (the higher the grade, the slighter the damage)
9: normal growth, as untreated plants The results are shown in Table 3.

TABLE 3

| Plant | Compound | Rate of application | Action |
|---|---|---|---|
| Avena sativa | 2 | 4 kg/ha | 6 |
|  | 3 | 4 kg/ha | 7 |
| Sinapis alba | 2 | 4 kg/ha | 1 |
|  | 3 | 4 kg/ha | 2 |
| Setaria italica | 2 | 4 kg/ha | 1 |
|  | 3 | 4 kg/ha | 1 |
| Stellaria media | 2 | 4 kg/ha | 1 |
|  | 3 | 4 kg/ha | 4 |

EXAMPLE 4

Postemergence herbicidal action (contact herbicide)

A number of weeds, both mono- and dicotyledonous, are sprayed postemergence in the 4- to 6-leaf stage with an aqueous active ingredient dispersion at a rate of 4 kg of test compound per hectare and kept at 24°–26° C. and 45–60% relative humidity. The test is evaluated 15 days later in accordance with the rating indicated above. The results are shown in Table 4.

TABLE 4

| Plant | Compound | Rate of application | Action |
|---|---|---|---|
| Avena sativa | 2 | 4 kg/ha | 1 |
|  | 3 | 4 kg/ha | 2 |
| Setaria italica | 2 | 4 kg/ha | 1 |
|  | 3 | 4 kg/ha | 1 |
| Lolium perenne | 2 | 4 kg/ha | 1 |
|  | 3 | 4 kg/ha | 2 |
| Solanum Pycopersicum | 2 | 4 kg/ha | 1 |
|  | 3 | 4 kg/ha | 1 |
| Sinapis alba | 2 | 4 kg/ha | 1 |
|  | 3 | 4 kg/ha | 1 |
| Stellaria media | 2 | 4 kg/ha | 1 |
|  | 3 | 4 kg/ha | 1 |

TABLE 4-continued

| Plant | Compound | Rate of application | Action |
|---|---|---|---|
| Phaseolus vulgaris | 1 | 4 kg/ha | 1 |
|  | 1 | 4 kg/ha | 1 |

EXAMPLE 5

Preemergence herbicidal action

Plastic pots are filled with expanded vermiculite (density: 0.135 g/cm$^3$; water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: *Nasturtium officinalis, Agrostis tenuis, Stellaria media* and *Digitaria sanguinalis*. The pots are then kept in a climatic chamber at 20° C., an illumination of about 20 klux and a relative humidity of 70%. During the germinating phase of 4 to 6 days, the pots are covered with lightpermeable material and watered with deionised water to increase the local humidity. After the 5th day, 0.5% of a commercial liquid fertiliser (Greenzit ®) is added to the water. The test is evaluated 12 days after sowing and the action on the test plants is assessed. The test compounds of Table 1 exhibit good to very good herbicidal activity in this test.

EXAMPLE 6

Herbicidal action in wild rice (paddy rice)

The weeds *Echinocloa crus galli* and *Monocharia vag.*, which occur in water, are sown in plastic beakers (surface: 60 cm$^2$; volume: 500 ml). After sowing, the beakers are filled with water up to the surface of the soil. 3 days after sowing, the water level is increased to slightly above the surface (3–5 mm). Application is effected 3 days after sowing by spraying the beakers with an aqueous emulsion of the test compounds. The rate of application corresponds to a concentration of 0.5 kg of active ingredient per hectare (concentration of the spray mixture=550 l/ha). The beakers are then kept in the greenhouse under optimum growth conditions for rice weeds, i.e. at 25°–30° C. and at high humidity. The evaluation of the tests takes place 3 weeks after application. The state of the plants is assessed in accordance with the rating indicated above. The results are shown in Table 5 below.

TABLE 5

| Plant | Compound | Rate of application | Action |
|---|---|---|---|
| Echinochloa crus galli | 2 | 0.5 kg/ha | 1 |
|  | 3 | 0.5 kg/ha | 1 |
| Monocharia vaginalis | 2 | 0.5 kg/ha | 1 |
|  | 3 | 0.5 kg/ha | 1 |

EXAMPLE 7

Desiccation and defoliation action

Cotton plants of the Deltapine variety are reared in earthen-ware pots in a greenhouse. After the capsules have formed, the plants are sprayed with an aqueous formulation of compound No. 1 at rates of application corresponding to 1.2, 0.6 and 0.3 kg/ha in field application. Untreated plants act as controls. Evaluation of the test is made 3, 7 and 14 days after application of the active ingredient by determining the degree of defoliation (percentage of fallen leaves) and of desiccation (drying out of the leaves remaining on the plant).

In this test, plants treated with test compounds of Table 1 at rates of application of 0.6 and 1.2 kg/ha are left after 7 days with only a few dried out leaves (>80% defoliation and dessication). Compound 3 exhibits the best activity.

EXAMPLE 8

Growth inhibition of tropical leguminous cover crops

The test plants (*Centrosema plumieri* and *Centrosema pubescens*) are reared until fully grown and then cut back to a height of 60 cm. The plants are sprayed 7 days later with an aqueous emulsion of the test compound. The test plants are kept at 70% relative humidity and 6000 lux artificial light for 14 hours per day, at day temperatures of 27° C. and night temperatures of 21° C. The test is evaluated 4 weeks after applications by assessing and weighing the new growth compared with controls and by determining the phytotoxicity.

In this test, a marked reduction in new growth of the plants treated with compounds of Table 1 at concentrations of 50 to 3000 g/ha is observed (less than 20% of the new growth of untreated control plants), without damage being caused to the test plants.

EXAMPLE 9

Growth regulation of soybeans

Soybeans of the "Hark" variety are sown in plastic containers in an earth/peat/sand mixture (6:3:1). The containers are put into a climatic chamber and the plants develop to the 5-6 trefoil leaf stage after about 5 weeks by optimum control of temperature, light, fertiliser addition, and watering. The plants are then sprayed with an aqueous mixture of a compound of formula I until thoroughly wetted. The concentration corresponds to up to 100 g a.i. per hectare. Evaluation is made about 5 weeks after application. Compared with untreated controls, the compounds of Table 1 of the invention markedly increase the number and weight of the harvested siliquae on the leading shoot.

EXAMPLE 10

Growth inhibition of cereals

Summer barley (*Hordeum vulgare*) and summer rye (*Secale*) are sown in sterilised soil in plastic beakers in a greenhouse and watered as required. The cereal shoots are treated about 21 days after sowing with an aqueous spray mixture of a compound of Table 1. The concentration corresponds to up to 100 g of active ingredient per hectare. Evaluation of the growth of the cereals is made 21 days after application. A comparison with untreated controls shows that the new growth of treated cereal plants is reduced (60-90% of the controls) and that the diameter of the stalks has in some cases increased.

EXAMPLE 11

Growth inhibition of grasses

Seeds of the grasses *Lolium perenne, Poa pratensis, Festuca ovina, Dactylis glomerate* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of Table 1. The concentration of test compound corresponds to a rate of application of up to 500 g a.i. per hectare. The growth of the grasses is evaluated 21 days after application. The test compounds of Table 1 effect a reduction in new growth in the range of 10-30% in comparison with untreated controls.

What is claimed is:

1. A 5-(N-3,4,5,6-tetrahydrophthalimido)benzoic acid ester of formula Ia

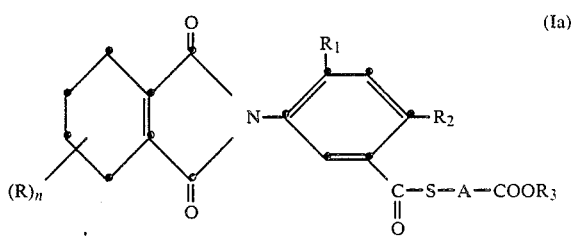

wherein
n is 0, 1 or 2,
R is $C_1$-$C_3$alkyl,
$R_1$ is halogen,
$R_2$ is halogen,
A is a straight chain or branched chain $C_1$-$C_4$alkylene bridge,
$R_3$ is $C_1$ to $C_4$alkyl, $C_3$-$C_6$alkenyl, $C_3$-$C_6$alkynyl or $C_3$-$C_7$cycloalkyl each of which may be unsubstituted or substituted by halogen or $C_1$-$C_4$alkoxy.

2. A compound selected from among
1-isopropoxycarbonyleth-1-ylthio 5-(N-3,4,5,6-tetrahydrophthalimido)-2-chloro-4-fluorobenzoate,
1-ethoxycarbonyleth-1-ylthio 5-(N-3,4,5,6-tetrahydrophthalimido)-2-chloro-4-fluorobenzoate,
cyclohexyloxycarbonylmethylthio 5-(N-3,4,5,6-tetrahydrophthalimido)-2-chloro-4-fluorobenzoate,
n-butoxycarbonylmethylthio 5-(N-3,4,5,6-tetrahydrophthalimido)-2-chloro-4-fluorobenzoate,
methoxyethoxycarbonylmethylthio 5-(N-3,4,5,6-tetrahydrophthalimido)-2-chloro-4-fluorobenzoate,
methoxycarbonylmethylthio 5-(N-3,4,5,6-tetrahydrophthalimido)-2-chloro-4-fluorobenzoate,
isopropoxycarbonylmethylthio 5-(N-3,4,5,6-tetrahydrophthalimido)-2-chloro-4-fluorobenzoate,
ethoxycarbonylmethylthio 5-(N-3,4,5,6-tetrahydrophthalimido)-2-chloro-4-fluorobenzoate,
methoxycarbonyleth-1-ylthio 5-(N-3,4,5,6-tetrahydrophthalimido)-2-chloro-4-fluorobenzoate,
allyloxycarbonyleth-1-ylthio 5-(N-3,4,5,6-tetrahydrophthalimido)-2-chloro-4-fluorobenzoate and
propinyloxycarbonylmethylthio 5-(N-3,4,5,6-tetrahydrophthalimido)-2-chloro-4-fluorobenzoate, according to claim 1.

3. A herbicidal and plant growth regulating composition which contains, as active ingredient, an effective amount of a 5-(N-3,4,5,6-tetrahydrophthalimido)benzoic acid ester according to claim 1, together with carriers and/or other adjuvants.

4. A method of selectively controlling weeds pre- or postemergence in crops of useful plants, which method comprises treating said useful plants or the crop area thereof with an effective amount of a compound according to claim 1, or of a composition containing such a compound.

* * * * *